US005783545A

United States Patent [19]

Paatz et al.

[11] Patent Number: 5,783,545
[45] Date of Patent: Jul. 21, 1998

[54] ENZYME PREPARATION CONTAINING A SILVER CORROSION INHIBITOR

[75] Inventors: Kathleen Paatz; Wilfried Raehse; Juergen Haerer, all of Duesseldorf, Germany; Werner Pichler, Kundl, Austria; Birgit Burg, Alpen, Germany

[73] Assignee: Henkel Kommanditgesellschaft auf Aktien, Duesseldorf, Germany

[21] Appl. No.: 663,301

[22] PCT Filed: Dec. 14, 1994

[86] PCT No.: PCT/EP94/04152

§ 371 Date: Jul. 24, 1996

§ 102(e) Date: Jul. 24, 1996

[87] PCT Pub. No.: WO95/17493

PCT Pub. Date: Jun. 29, 1995

[30] Foreign Application Priority Data

Dec. 23, 1993 [DE] Germany .................. 43 44 215.3

[51] Int. Cl.$^6$ .................. C11D 3/00; C11D 7/18; C11D 7/54
[52] U.S. Cl. .................. 510/305; 510/226; 510/320; 510/335; 510/374; 510/392; 510/451
[58] Field of Search .................. 510/226, 305, 510/320, 335, 374, 392, 451

[56] References Cited

U.S. PATENT DOCUMENTS

| | | | |
|---|---|---|---|
| 3,549,539 | 12/1970 | Mallows | 252/99 |
| 3,623,956 | 11/1971 | Kalabokias | 195/66 R |
| 3,784,476 | 1/1974 | van Kampen et al. | 252/109 |
| 4,009,076 | 2/1977 | Green et al. | 195/63 |
| 4,264,738 | 4/1981 | Stepanov et al. | 435/222 |
| 4,751,003 | 6/1988 | Raehse et al. | 210/639 |

FOREIGN PATENT DOCUMENTS

| | | |
|---|---|---|
| 006638 | 1/1980 | European Pat. Off. . |
| 135226 | 3/1985 | European Pat. Off. . |
| 135227 | 3/1985 | European Pat. Off. . |
| 200032 | 11/1986 | European Pat. Off. . |
| 0290223 | 11/1988 | European Pat. Off. . |
| 0415652 | 3/1991 | European Pat. Off. . |
| 1803099 | 5/1969 | Germany . |
| 1617232 | 2/1971 | Germany . |
| 2101803 | 7/1971 | Germany . |
| WO9102792 | 3/1991 | WIPO . |
| WO9211347 | 7/1992 | WIPO . |
| WO9426859 | 11/1994 | WIPO . |
| WO9426860 | 11/1994 | WIPO . |

*Primary Examiner*—Mukund J. Shah
*Assistant Examiner*—Brenda Coleman
*Attorney, Agent, or Firm*—Ernest G. Szoke; Wayne C. Jaeschke; Daniel S. Ortiz

[57] ABSTRACT

The invention provides an enzyme containing granule with a coating containing a silver corrosion inhibitor. The particle is formed from a core containing a first enzyme and an organic or inorganic carrier which can be coated with a second particulate enzyme. The core is coated with a coating containing at least one salt of manganese, titanium, zirconium, hafnium, vanadium, cobalt and cerium. A method for preparing the granule is also disclosed.

20 Claims, No Drawings

ENZYME PREPARATION CONTAINING A SILVER CORROSION INHIBITOR

This application is a 371 of PCT/EP94/04152, filed Dec. 14, 1994, which is a PCT application claiming priority of German P 43 44 215.3, filed Dec. 23, 1993.

FIELD OF THE INVENTION

This invention relates to enzyme granules containing a silver corrosion inhibitor, to a process for their production and to the use of the granules in solid cleaning formulations, more especially for machine dishwashing.

RELATED ART

Enzymes, more especially proteases, are widely used in detergents, washing aids and cleaning compositions. Normally, the enzymes are not used as concentrates, but rather in the form of mixtures with a diluent and carrier material. If corresponding enzyme preparations are mixed with typical detergents or cleaning compositions, a considerable reduction in enzyme activity can occur in storage, especially if bleaching-active compounds are present. Application of the enzymes to carrier salts and granulation in accordance with DE-OS 16 17 190 or by "bonding" with nonionic surfactants in accordance with DE-OS 16 17 118 or with aqueous solutions of cellulose ethers in accordance with DE-OS 17 87 568 does not lead to a significant improvement in storage stability because the sensitive enzymes in such mixtures are generally present on the surface of the carrier substance. Although the stability of the enzymes in storage can be significantly increased by coating the enzymes with or encapsulating them in the carrier material and then converting them into the required particle form by extrusion, pressing and marumerizing, as described, for example in DE-PS 16 17 232, in DE-OS 20 32 768 and in DE-ASS 21 37 042 and 21 37 043, the resulting enzyme preparations show inadequate solubility properties. The undissolved particles can become trapped in, and soil, the articles to be cleaned or pass unused into the wastewater. Although the encapsulating compositions known from DE-OS 18 03 099, which consist of a mixture of solid acids or acidic salts and carbonates or bicarbonates and which disintegrate on addition of water, improve solubility, they are in turn extremely sensitive to moisture and, accordingly, necessitate additional protective measures.

EP 168 526 describes enzyme granules which contain water-swellable starch, zeolite and a water-soluble granulation aid. This document proposes a production process for such formulations which essentially comprises concentrating a fermenter solution freed from insoluble constituents, adding the additives mentioned, granulating the resulting mixture and optionally coating the granules with film-forming polymers and dyes. The process with the additive mixture proposed therein is advantageously carried out with fermentation solutions which have been concentrated to a relatively high dry matter content, for example 55% by weight. In addition, the granules thus produced have such a high dissolving or disintegration rate under in-use conditions that some of them even disintegrate relatively rapidly in storage, so that the enzymes are deactivated.

International patent application WO 92/11347 describes enzyme granules for use in granular detergents and cleaning compositions containing 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. By virtue of this mixture of additives, the enzyme can be processed without any significant loss of activity, in addition to which the stability of the enzymes in storage in the granules is satisfactory.

Another problem, especially for machine dishwashing detergents, is the need to incorporate corrosion inhibitors for table silver in cases where the detergents contain the oxygen-based bleaching or oxidizing agents which have recently been introduced as standard ingredients. Silver can react on cleaning with sulfur-containing substances dissolved or dispersed in the rinsing water because food residues, including inter alia mustard, peas, egg and other sulfur-containing compounds, such as mercaptoamino acids, are introduced into the wash liquor in the washing of crockery in domestic dishwashing machines. The far higher temperatures in machine dishwashing and the relatively long contact times with the sulfur-containing food remains also promote the tarnishing of silver by comparison with manual dishwashing. In addition, the silver surface is completely degreased by the intensive cleaning process in the dishwashing machine so that it becomes more sensitive to chemical influences.

The problem of the tarnishing of silver becomes particularly acute when, as an alternative to the active chlorine compounds which oxidatively "deactivate" sulfur-containing substances, active oxygen compounds, for example sodium perborate or sodium percarbonate, are used to eliminate bleachable soils, for example tea stains/tea coatings, coffee residues, dyes from vegetables, lipstick remains and the like.

These active oxygen compounds are used above all in modern low-alkali machine dishwashing detergents of the new generation, generally in conjunction with bleach activators. These dishwashing detergents generally consist of the following functional components: builder (complexing agent/dispersant), alkali carrier, bleaching system (bleaching agent+bleach activator), enzyme and surfactant. Under the dishwashing conditions prevailing where detergents such as these are used, not only are sulfidic coatings formed in the presence of silver, oxidic coatings are also formed on the silver surfaces through the oxidizing attack of the peroxides formed as intermediates or rather the active oxygen.

The avoidance of silver corrosion, i.e. the formation of sulfidic, oxidic or chloridic coatings on silver, is the subject of numerous publications. Alkaline dishwashing detergents containing benzotriazoles as corrosion inhibitor for silver are known from GB 1,131,738. U.S. Pat. No. 3,549,539 describes highly alkaline machine dishwashing detergents which may contain inter alia perborate with an organic bleach activator as oxidizing agent. Additions of benzotriazole and even iron(III) chloride are also recommended to prevent tarnishing. EP 135 226 and EP 135 227 describe mildly alkaline machine dishwashing detergents containing peroxy compounds and activators in which benzotriazoles and fatty acids may be present as silver corrosion inhibitors. Finally, it is known from DE-OS 41 28 672 that peroxy compounds activated by addition of known organic bleach activators prevent the tarnishing of silver in strongly alkaline detergents. Hitherto unpublished German patent applications DE 43 25 922.7 and DE 43 15 397.6 describe the use of titanium, zirconium, hafnium, vanadium, cobalt or cerium salts and/or complexes, in which the metals are present in one of the oxidation stages II, III, IV, V or VI, or of manganese(II) salts or complexes for preventing the corrosion of silver. Even though the detergents mentioned above are by no means complex in their composition, efforts have nevertheless been made to use components containing more than one of the active substances mentioned above (builder, alkali carrier, bleaching system, enzyme, surfactant, silver corrosion inhibitor) in their production.

Accordingly, the problem addressed by the present invention was to develop a process with which it would be possible readily to produce enzyme-containing granules which would additionally contain a corrosion inhibitor for silver, for example in the form of certain inorganic salts, in which the components mentioned, especially the enzyme, would be stable in storage.

BRIEF SUMMARY OF THE INVENTION

Accordingly, the present invention relates to enzyme granules suitable for incorporation in, in particular, particulate detergents and containing as core enzyme and inorganic and/or organic carrier material and optionally granulation aids to which a uniform coating is applied, characterized in that the coating contains a silver corrosion inhibitor, more especially an inorganic silver corrosion inhibitor. Manganese, titanium, zirconium, hafnium, vanadium, cobalt or cerium salts and/or complexes, in which the metals mentioned are present in one of the oxidation stages II, III, IV, V or VI, are preferred.

DETAILED DESCRIPTION OF THE INVENTION

The word "corrosion" is meant to be interpreted in its broadest chemical sense. More particularly, "corrosion" in the context of the invention is intended to stand for any visually just discernible change in a metal surface, in the present case silver, whether for example in the form of local discoloration or, for example, in the form of tarnishing over a large area.

The metal salts or metal complexes preferably used as silver corrosion inhibitors should be at least partly soluble in water. The counterions suitable for salt formation include any typical inorganic anions with one, two or three negative charges, for example oxide, sulfate, nitrate, fluoride, and also organic anions, for example stearate.

Metal complexes in the context of the invention are compounds which consist of a central atom and one or more ligands and optionally one or more of the anions mentioned above. The central atom is one of the metals mentioned above in one of the oxidation stages mentioned above. The ligands are neutral molecules or anions which may be mono- or multi-dentate. The term "ligand" as used in the context of the present invention is explained, for example, in Römpp "Chemie Lexikon", Georg Thieme Verlag, Stuftgart/N.Y., 9th Edition, 1990, page 2507. If, in a metal complex, the charge of the central atom and the charge of the ligand(s) do not add up to zero, either one or more of the anions mentioned above or one or more cations, for example sodium, potassium, ammonium ions, provide for charge equalization, depending on whether an excess cationic charge or an excess anionic charge is present.

Preferred metal salts and/or metal complexes are $MnSO_4$, $V_2O_5$, $V_2O_4$, $VO_2$, $TiOSO_4$, $K_2TiF_6$, $K_2ZrF_6$, $CoSO_4$, $Co(NO_3)_2$ $Ce(NO_3)_3$ and mixtures thereof. These metal salts or metal complexes are commercial substances which may be used for protecting silver against corrosion without preliminary cleaning. For example, the mixture of pentavalent and tetravalent vanadium ($V_2O_5$, $VO_2$, $V_2O_4$,) known from the production of $SO_3$ (contact process) is suitable as is the titanyl sulfate $TiOSO_4$ formed by diluting a $Ti(SO_4)_2$ solution with water.

In a preferred embodiment, the enzyme granules contain 40% by weight to 95% by weight and more particularly 50% by weight to 85% by weight of enzyme-containing core and 5% by weight to 60% by weight and more particularly 15% by weight to 50% by weight of coating layer. The entire coating layer may consist of the silver corrosion inhibitor. In one preferred embodiment of the enzyme granules according to the invention, however, the coating layer of the enzyme-containing core consists of a coating system which contains 45% by weight to 90% by weight and more especially 50% by weight to 80% by weight of silver corrosion inhibitor, up to 25% by weight and more particularly 5% by weight to 20% by weight of fine-particle inorganic pigment, 5% by weight to 20% by weight of an alcohol solid at room temperature with a melting point of 45° C. to 65° C., up to 5% by weight and, more particularly, 1% by weight to 3% by weight of emulsifier for the alcohol, up to 5% by weight and, more particularly, 0.2% by weight to 3% by weight of dispersant for the silver corrosion inhibitor or the inorganic pigment and up to 7% by weight of water.

The enzyme-containing core may be prepared by any known method using any carrier materials compatible with the enzyme. At least partly for reasons of greater enzyme stability, it is preferably produced by the process according to International patent application WO 92/11347 or German patent application DE 43 10 506.8, which comprises an extrusion step, using swellable starch, water-soluble organic polymer and cereal flour.

Accordingly, the present invention also relates to a process for the production of enzyme granules with an average particle size of 0.8 mm to 1.2 mm suitable for incorporation in particulate detergents by extrusion of an enzyme compound prepared by mixing of a concentrated fermentation broth optionally freed beforehand from insoluble constituents by microfiltration with inorganic and/or organic carrier material as additive, optionally spheronization of the extrudate in a spheronizer, drying and application of an outer coating layer, an outer coating layer of a coating system of at least 50% by weight of silver corrosion inhibitor, up to 25% by weight and, more particularly 5% by weight to 20% by weight of fine-particle inorganic pigment, 5% by weight to 20% by weight of alcohol solid at room temperature with a melting point of 45° C. to 65° C., up to 5% by weight and, more particularly, 1% by weight to 3% by weight of emulsifier for the alcohol, up to 5% by weight and, more particularly, 0.2% by weight to 3% by weight of dispersant for the silver corrosion inhibitor or the inorganic pigment and up to 7% by weight of water being applied in a fluidized bed of extrudate. In one preferred embodiment of this process, an enzyme core produced by extrusion is mixed with a particulate second enzyme and optionally other particulate enzymes under agglomeration conditions, optionally in the presence of a binder, and the coating containing the silver corrosion inhibitor is subsequently or simultaneously applied, the average particle size of the extrudate core containing the first enzyme preferably being 1.1 to 3 times and, more particularly, 1.3 to 2 times the average particle size of the second or further particulate enzyme(s). This variant is based on the production process for multi-enzyme granules which is disclosed in German patent application DE 43 29 463.4. The enzyme in the extrudate core is preferably protease while the enzyme or—where several different smaller particles are used— enzymes present in the separately produced, smaller particles which agglomerate onto the extrudate is/are amylase, lipase, cellulase and/or oxidase.

The alcohol component of the coating system is preferably a primary linear alcohol containing 14 to 22 carbon atoms or a mixture thereof. The alcohols mentioned include in particular myristyl alcohol, cetyl alcohol, stearyl alcohol, arachidyl alcohol, behenyl alcohol and monounsaturated to triunsaturated alcohols of corresponding chain length. It is essential that the alcohol component of the coating system have a melting point of 45° C. to 65° C. and, more particularly, in the range from 50° C. to 60° C., the expression "melting point" in the context of the present invention being the temperature at which 100% of the alcohol component is present in liquid form on heating. Where alcohol mixtures are used, it is even possible to use those containing small amounts, normally less than 15% by weight, based on the alcohol mixture, of components liquid at room temperature providing the alcohol mixture as a whole appears solid at room temperature and has a solidification point in the range from 45° C. to 65° C. and more particularly in the range from 50° C. to 60° C. The solidification point is the temperature at which solidification occurs on cooling to a temperature above the melting point of heated material. It may be determined with a rotating thermometer by the method according to DIN ISO 2207.

Suitable emulsifiers for the alcohol component are substances which are capable of emulsifying the alcohol component in water, so that a mixture sprayable at temperatures of up to 95° C. is formed, and/or which enable the coating system to be converted into a homogeneous melt sprayable at temperatures of up to 120° C. A reference point in this regard can be that liquids with viscosities of up to about 10,000 cPs can generally be sprayed and applied to enzyme granules without difficulty at the temperatures mentioned by means of suitable equipment. Emulsifiers for the alcohol component of the coating system include, for example, the ethoxylation products of the alcohols mentioned, their reaction products with on average 25 to 80 mole equivalents and more particularly 30 to 45 mole equivalents of ethylene oxide being preferred. If the coating system is applied to the enzyme granules as an aqueous dispersion, compounds with degrees of ethoxylation of 25 to 50, i.e. reaction products with 25 to 50 mole equivalents of ethylene oxide, are preferred among the compounds mentioned above. Alternatively to or in addition to the alcohol ethoxylates, ethoxylated fatty acids, the degree of ethoxylation preferably being 3 to 9, ethoxylated fatty acid amides, the degree of ethoxylation preferably being 4 to 11, and/or ethoxylation products of hydroxyfatty acid esters containing 1 to 6 carbon atoms in the alcohol part of the ester, for example ricinoleic acid glyceride, the degree of ethoxylation preferably being 5 to 80 and more particularly 20 to 40, may also be used as emulsifier component in the coating system. The fatty acid component of the substances mentioned preferably contains 12 to 22 carbon atoms. If desired, the ethoxy groups in the emulsifiers mentioned may be at least partly replaced by propoxy groups.

The inorganic pigments with which any disturbing coloration in the enzyme granules can be masked include, for example, calcium carbonate, titanium dioxide, which may be present in the rutile or anatase crystal modification, zinc oxide, zinc sulfide, white lead (basic lead carbonate), barium sulfate, aluminium hydroxide, antimony oxide, lithopone (zinc sulfide/barium sulfate), kaolin, chalk and/or mica. The inorganic pigments are present in such fine-particle form that they may be dispersed in a melt of the organic components of the coating system or in water. The average particle size of such pigments is normally in the range from 0.004 µm to 50 µm. If, in particular, the pigment or the coating system as a whole is to be used in the form of an aqueous dispersion, this dispersion preferably contains dispersants for the pigment and/or the silver corrosion inhibitor. The dispersant used may be inorganic, for example aluminium oxide or silicon oxide, which may also serve as pigments, or organic, for example diethylene glycol or dipropylene glycol. Pigments surface-modified with dispersants may also be used. Titanium dioxide pigment, more especially in rutile form, surface-modified with Al, Si, Zr or polyol compounds, as marketed for example under the name of Kronos® 2132 (by Kronos-Titan) or under the name of Hombitan® R 522 (by Sachtleben Chemie GmbH), is preferably used. The Tiona® RLL, AG and VC types marketed by Solvay and the Bayertitan® RD, R-KB and AZ types marketed by Bayer AG are also suitable.

Suitable enzymes are above all the proteases, lipases, amylases and/or cellulases obtained from microorganisms, such as bacteria or fungi, proteases produced from bacillus species and mixtures thereof with amylases being preferred. They are obtained in known manner by fermentation processes from suitable microorganisms which are described, for example, in DE-OSS 19 40 488, 20 44 161, 22 01 803 and 21 21 397, in U.S. Pat. Nos. 3,632,957 and 4,264,738 and in European patent application EP 006 638. The process according to the invention may be used with particular advantage for the formulation of highly active proteases, which are known for example from International patent application WO 9112792, because their stable incorporation in detergents often presents difficulties and the formation of unwanted enzyme dusts is avoided in accordance with the invention. Enzymes are present in the granules according to the invention in quantities of preferably 4% by weight to 20% by weight. If the enzyme granules according to the invention are a protease-containing formulation, their protease activity is preferably in the range from 150,000 protease units (PU, as determined by the method described in Tenside 7 (1970), 125) to 350,000 PU and more particularly in the range from 160,000 PU to 300,000 PU per gram of enzyme granules.

In principle, suitable carrier materials for the enzyme are any organic or inorganic powder-form materials which destroy or deactivate the enzymes to be granulated to only a negligible extent, if at all, and which are stable under granulation conditions. Materials such as these include, for example, starch, cereal flour, cellulose powder, alkali alumosilicate, more especially zeolite, layer silicate, for example bentonite or smectite, and water-soluble inorganic or organic salts, for example alkali metal chloride, alkali metal sulfate, alkali metal carbonate or alkali metal acetate, sodium or potassium being the preferred alkali metals. A mixture of water-swellable starch, cereal flour and optionally cellulose powder and also alkali metal carbonate is preferably used as the carrier material.

The water-swellable starch is preferably corn starch, rice starch, potato starch or mixtures thereof, corn starch being particularly preferred. Swellable starch is present in the enzyme granules according to the invention in quantities of preferably 20 to 50% by weight and, more preferably, 25 to 45% by weight. The sum total of the quantities of swellable starch and flour is preferably not more than 80% by weight and, more particularly, is in the range from 32% by weight to 65% by weight.

The cereal flour is in particular a product obtainable from wheat, barley, rye or oats or a mixture of these flours, whole-grain flours being preferred. A whole-grain flour is understood to be a flour which has not been fully ground and which has been produced from whole, non-excorticated grains or which consists at least predominantly of such a product, the rest consisting of fully ground flour or starch.

Commercial wheat flours, such as type 450 or type 550, are preferably used. Flour products of the cereals leading to the swellable starches mentioned above may also be used providing the flours have been produced from the whole grains. It is known that the flour component of the additive mixture enables the odor of the enzyme preparation to be significantly reduced to a level which exceeds by far the reduction in odor achieved by the incorporation of equal quantities of corresponding starches. The cereal flour is present in the enzyme granules according to the invention in quantities of preferably 10 to 35% by weight and more preferably 15 to 25% by weight.

The enzyme granules according to the invention preferably contain 1 to 50% by weight and preferably 5 to 25% by weight, based on the granules as a whole, of a granulation auxiliary system containing alkali metal carboxymethyl cellulose with degrees of substitution of 0.5 to 1 and polyethylene glycol and/or alkyl polyethoxylate as a further component of the carrier material. This granulation auxiliary system preferably contains 0.5% by weight to 5% by weight of alkali metal carboxymethyl cellulose with degrees of substitution of 0.5 to 1 and up to 3% by weight of polyethylene glycol and/or alkyl polyethoxylate, based on the final enzyme granules. In a particularly preferred embodiment, at least 0.5% by weight and, more particularly, 0.8% by weight to 2% by weight of polyethylene glycol with an average molecular weight below 1,000 and/or alkyl polyethoxylate containing at least 30 ethoxy groups is present where the granulation auxiliary system contains more than 2% by weight of alkali metal carboxymethyl cellulose.

Other cellulose or starch ethers, such as carboxymethyl starch, methyl cellulose, hydroxyethyl cellulose, hydroxypropyl cellulose and corresponding cellulose mixed ethers, gelatine, casein, tragacanth, maltodextrose, sucrose, invert sugar, glucose sirup or other water-soluble or readily water-dispersible oligomers or polymers of natural or synthetic origin, may optionally be used as additional components of the granulation auxiliary system. Suitable synthetic water-soluble polymers are polyacrylates, polymethacrylates, copolymers of acrylic acid with maleic acid or compounds containing vinyl groups and also polyvinyl alcohol, partly hydrolyzed polyvinyl acetate and polyvinyl pyrrolidone. If the compounds mentioned above are compounds containing free carboxyl groups, they are normally present in the form of their alkali metal salts, more especially their sodium salts. These additional granulation auxiliaries may be present in the enzyme granules according to the invention in quantities of up to 10% by weight and, more especially, in quantities of 0.5% by weight to 8% by weight. Although polyethylene glycols of relatively high molecular weight, i.e. those with an average molecular weight above 1,000, may be used as synthetic water-soluble polymers with a dust-binding effect, the relatively high molecular weight polyethylene glycols produce an undesirable increase in the necessary granule dissolving time so that these substances are preferably absent altogether from the enzyme granules according to the invention.

The enzyme granules according to the invention are preferably produced from fermenter broths which have been freed from insoluble constituents, for example by microfiltration. The microfiltration is preferably carried out by crossflow microfiltration using porous tubes with micropores larger than 0.1 μm in size, flow rates of the concentrate solution of more than 2 m/s and a pressure difference to the permeate side of less than 5 bar, as described for example in European patent application EP 200 032. The microfiltration permeate is then concentrated, preferably by ultrafiltration, optionally followed by evaporation by concentration in vacuo. The concentration step may be carried out in such a way that only relatively low dry matter contents of preferably 5% by weight to 50% by weight and, more preferably, 10% by weight to 40% by weight are obtained, as described in International patent application WO 92/11347. The concentrate is best added to a dry powder-form to granular mixture of the above-described additives prepared beforehand. The water content of the mixture should be selected in such a way that, during compounding with stirring and beating tools, the mixture can be converted into particles which are non-tacky at room temperature and then deformed and extruded by application of relatively high pressures. The free-flowing compound is then processed in known manner in a kneader and an adjoining extruder to form a plastic, substantially homogeneous paste which can be heated to temperatures of 40° to 60° C. and, more particularly to temperatures of 45° to 550° C. as a result of mechanical compounding. The material leaving the extruder is passed through a multiple-bore extrusion die followed by a cutting blade and is thus size-reduced to cylindrical particles of defined size. The bore diameter of the multiple-bore die is best between 0.7 mm and 1.2 mm and preferably between 0.8 mm and 1.0 mm. The particles present in this form may then be dried and coated with the coating system according to the invention. However, it has proved to be of advantage to spheronize the cylindrical particles leaving the extruder and cutting unit before they are coated, i.e. to spheronize and smooth them in suitable machines. A machine consisting of a cylindrical vessel with fixed side walls and a friction plate rotatably mounted at its base is used for this purpose. Machines of this type are commercially available under the name of Marumerizer® and are described, for example, in DE-ASS 21 37 042 and 21 37 043. Any dust-form fractions below 0.1 mm in size, more particularly below 0.4 mm in size, and any coarse fractions larger than 2 mm in size and, more particularly, larger than 1.6 mm in size may then be removed by sieving or air separation and optionally returned to the production process. After spheronizing, the microspheres are dried continuously or in batches, preferably in a fluidized-bed dryer, at feed air temperatures of, preferably, 35° to 50° C. and, more particularly, at a product temperature of not more than 42° C., to the required residual moisture content of, for example, 4% by weight to 10% by weight and, more particularly, 5% by weight to 8% by weight, based on the granules as a whole.

The coating system containing the silver corrosion inhibitor is applied as an outer coating after or preferably during the drying step. In one embodiment of the production process according to the invention, the coating system is introduced into the fluidized bed of enzyme-containing core as an aqueous solution or dispersion preferably containing 30% by weight to 65% by weight of water and 35% by weight to 70% by weight of the coating system, the coating system containing in particular 1 % by weight to 2.5% by weight, based on the system as a whole, of dispersant for the silver corrosion inhibitor and/or the pigment. The water introduced through the aqueous dispersion is removed again during the simultaneous drying step or during a subsequent drying step. In another embodiment of the production process according to the invention, the coating system is applied to the enzyme-containing core, optionally with cooling, as a heated liquid present at a temperature of 5° C. to 45° C. above the melting point of the alcohol component. These procedures may even be applied in combination, i.e. one part of the coating system preferably consisting solely of the silver corrosion inhibitor is applied in the form of an aqueous solution or dispersion while a second part preferably containing the other components of the coating system is applied in the form of a melt. In a preferred embodiment, the coating system is applied to the enzyme-containing extrudate as an outer coating layer in a quantity of 10% by weight to 50% by weight, based on the final granules.

The enzyme preparation obtained by the process according to the invention consists of substantially rounded, uniformly coated and dust-free particles which generally have an apparent density of around 500 to 900 grams per liter and, more particularly, 650 to 880 grams per liter. The granules according to the invention are distinguished by very high stability in storage, more particularly at temperatures above room temperature and at high atmospheric humidity levels, and by rapid dissolving behavior in the detergent liquor. For example, it is possible to produce granules according to the invention which release 100% of their enzyme activity in water at 25° C. within 3 minutes and, more particularly, within 90 seconds to 2 minutes.

The enzyme granules according to the invention or produced by the process according to the invention are preferably used for the production of solid, more especially particulate, detergents which can be obtained simply by mixing the enzyme granules with other powder components typically present in such detergents. For incorporation in particulate detergents, the enzyme granules preferably have average particle sizes of 0.8 mm to 1.6 mm. The granules according to the invention preferably contain less than 2% by weight and, in particular, at most 1.4% by weight of particles with particle sizes outside the 0.4 mm to 1.6 mm range.

Since, as mentioned above, the silver corrosion inhibitors are particularly suitable for preventing the corrosion of silver when present in low-alkali machine dishwashing detergents, the present invention also relates to a low-alkali machine dishwashing detergent of which a 1% by weight solution has a pH value of 8 to 11.5 and preferably 9 to 10.5 and which contains enzyme, silver corrosion inhibitor, from 15% by weight to 60% by weight and preferably from 30% by weight to 50% by weight of water-soluble builder component, from 5% by weight to 25% by weight and preferably from 10% by weight to 15% by weight of oxygen-based bleaching agent, from 1% by weight to 10% by weight and preferably from 2% by weight to 6% by weight of bleach activator, based in each case on the detergent as a whole, characterized in that it contains from 0.1% by weight to 10% by weight and, more particularly, from 0.5% by weight to 5% by weight of enzyme granules which, in their core, contain enzyme and inorganic and/or organic carrier material and optionally granulation auxiliaries and which have a uniform coating layer containing a silver corrosion inhibitor, more particularly an inorganic silver corrosion inhibitor. Manganese, titanium, zirconium, hafnium, vanadium, cobalt or cerium salts and/or complexes, in which the metals mentioned are present in one of the oxidation stages II, III, IV, V or VI, are also preferred.

In principle, any of the builders typically used in machine dishwashing detergents, for example polymeric alkali metal phosphates, which may be present in the form of their alkaline, neutral or acidic sodium or potassium salts, may be used as the water-soluble builder components in the low-alkali detergent according to the invention. Examples of such polymeric alkali metal phosphates are tetrasodium diphosphate, disodium dihydrogen diphosphate, pentasodium triphosphate, so-called sodium hexametaphosphate and the corresponding potassium salts or mixtures of sodium and potassium salts. They may be used in quantities of up to about 35% by weight, based on the detergent as a whole. However, the detergents according to the invention are preferably free from such phosphates. Other possible water-soluble builder components are, for example, organic polymers of native or synthetic origin, above all polycarboxylates, which act as co-builders, particularly in hard-water regions. Examples of these organic polymers include polyacrylic acids and copolymers of maleic anhydride and acrylic acid and also the sodium salts of these polymer acids. Commercial products are, for example, Sokalan® CP 5 and PA 30, products of BASF. Polymers of native origin suitable as co-builders include, for example, oxidized starch, for example according to German patent application P 42 28 786, and polyamino acids, such as polyglutamic acid or polyaspartic acid. Other possible builder components are naturally occurring hydroxycarboxylic acids such as, for example, monohydroxy and dihydroxy succinic acid, α-hydroxypropionic acid and gluconic acid. Preferred builder components include the salts of citric acid, more particularly sodium citrate. The sodium citrate used may be anhydrous trisodium citrate or, preferably, trisodium citrate dihydrate. Trisodium citrate dihydrate may be used in the form of a fine or coarse crystalline powder. Depending on the pH value ultimately established in the detergents according to the invention, the acids corresponding to the co-builder salts mentioned may also be present.

Suitable oxygen-based bleaching agents are, above all, sodium perborate monohydrate and tetrahydrate and/or sodium percarbonate. The use of sodium percarbonate has advantages insofar as it has a particularly favorable effect on corrosion behavior on glasses. Accordingly, the oxygen-based bleaching agent is preferably a percarbonate salt, more particularly sodium percarbonate. Since, in general, oxygen-based bleaching agents only develop their full effect at elevated temperatures, so-called bleach activators are used to activate them at around 60C, i.e. the approximate temperature of the dishwashing process in the dishwashing machine. Suitable bleach activators are, for example, pentaacetyl glucose, 1,5-diacetyl-2,2-dioxohexahydro-1,3,5-triazine (DADHT) and/or isatoic anhydride, although N,N, N',N'-tetraacetyl ethylenediamine (TAED) is preferably used. In addition, it can also be useful to add small quantities of known bleach stabilizers, for example phosphonates, borates or metaborates and metasilicates and also magnesium salts, such as magnesium sulfate.

The detergents according to the invention preferably contain the alkali carriers typically present in low-alkali machine dishwashing detergents, for example alkali metal silicates, alkali metal carbonates and/or alkali metal hydrogen carbonates. The alkali carriers typically used include carbonates, hydrogen carbonates and alkali metal silicates with a molar ratio of $SiO_2$ to $M_2O$ (M=alkali metal atom) of 1.5:1 to 2.5:1. Alkali metal silicates may be present in quantities of up to 30% by weight, based on the detergent as a whole. Highly alkaline metasilicates are preferably not used at all as alkali carriers. The alkali carrier system preferably used in the detergents according to the invention is a mixture of carbonate and hydrogen carbonate, preferably sodium carbonate and hydrogen carbonate, which is present in a quantity of up to 60% by weight and preferably in quantity of 10% by weight to 40% by weight. The ratio of carbonate used to hydrogen carbonate used varies according to the pH value ultimately required. However, an excess of sodium hydrogen carbonate is normally used so that the ratio by weight of hydrogen carbonate to carbonate is generally from 1:1 to 15:1.

In addition, the detergents according to the invention may contain enzymes made up in solid form, such as proteases, amylases, lipases and cellulases, which are not present in the form of the granules according to the invention, for example proteases, such as BLAP®, Optimase®, Opticlean®, Maxacal®, Maxapem®, Esperase® and/or Savinase®; amylases, such as Termamyl®, Amylase-LT® and/or Maxamyl®; lipases, such as Lipolase® and/or Lipozym®; cellulases, such as Celluzym® and/or KAC®.

Surfactants, more particularly low-foaming nonionic surfactants, may optionally be added to the detergents according to the invention to improve the removal of grease-containing food remains and to act as wetting agents and optionally as granulation auxiliaries in the production of the detergents. They may be present in quantities of up to 5% by weight and preferably in quantities of up to 2% by weight. Extremely low-foaming compounds are normally used and preferably include $C_{12-18}$ alkyl polyethylene glycol/polypropylene glycol ethers containing up to 8 moles of ethylene oxide and 8 moles of propylene oxide units in the molecule. However, it is also possible to use other nonionic surfactants known as low foamers, for example $C_{12-18}$ alkyl polyethylene glycol/polybutylene glycol ethers containing up to 8 moles of ethylene oxide and 8 moles of butylene oxide units in the molecule, endcapped alkyl polyalkylene glycol mixed ethers and the foaming, but ecologically attractive $C_{8-14}$ alkyl polyglucosides with a degree of polymerization of around 1 to 4 (for example APG® 225 and APG® 600, products of Henkel KGaA) and/or $C_{12-14}$ alkyl polyethylene glycols containing 3 to 8 ethylene oxide units in the molecule. Surfactants from the family of glucamides, for example alkyl-N-methyl glucamides, in which the alkyl moiety preferably emanates from a $C_{6-14}$ fatty alcohol, are also suitable. In some cases, it is of advantage to use the described surfactants in the form of mixtures, for example a mixture of alkyl polyglycoside with fatty alcohol ethoxylates or a mixture of glucamide with alkyl polyglycosides.

If the detergents foam too vigorously in use, up to 6% by weight and preferably around 0.5% by weight to 4% by weight of a foam-suppressing compound, preferably from the group of silicone oils, mixtures of silicone oil and hydrophobicized silica, paraffins, paraffin/alcohol mixtures, hydrophobicized silica, bis-fatty acid amides and other known commercially available foam inhibitors, may be added to them. Other optional ingredients in the detergents according to the invention are, for example, perfume oils.

The dishwashing detergents according to the invention are preferably present as powder-form, granular or tablet-form preparations which may be produced in known manner, for example by mixing, granulation, roll compacting and/or by spray drying of the heat-resistant component and addition of the more sensitive components, including in particular the enzyme granules according to the invention.

To produce detergents according to the invention in tablet form, all the components are preferably mixed together in a mixer and the resulting mixture is tabletted in conventional tablet presses, for example eccentric presses or rotary presses, under pressures of $200 \cdot 10^5$ Pa to $1,500 \cdot 10^5$ Pa. Breakage-resistant tablets with flexural strengths of normally more than 150N, which still dissolve sufficiently quickly under in-use conditions, are readily obtained in this way. Tablets produced in this way preferably weigh between 15 and 40 g and, more particularly, between 20 g and 30 g for a diameter of 35 mm to 40 mm.

The machine dishwashing detergents according to the invention may be produced in the form of non-dust-emitting, storable free-flowing powders and/or granules with high apparent densities of 800 to 1,000 g/l by mixing the builder components with at least some liquid mixture components in a first process step to increase the apparent density of the compound and then combining the other components of the machine dishwashing detergent, including the enzyme granules containing a silver corrosion inhibitor, with the compound thus obtained, if desired after intermediate drying.

The detergents may be used both in domestic dishwashing machines and in institutional dishwashing machines. They are added by hand or by suitable dispensing units. The in-use concentrations in the wash liquor are between about 2 and 8 g/l and preferably between 2 and 5 g/l.

The dishwashing program is generally augmented by a few intermediate rinse cycles with clear water after the main wash cycle and terminated by a final rinse cycle using a conventional rinse aid. Where the detergents according to the invention are used, not only completely clean and hygienically satisfactory dishes, but above all sparkling articles of silverware are obtained after drying.

EXAMPLES

Example 1

A harvest broth obtained after fermentation containing 75,000 protease units per g (PU/g), as described in International patent application WO 91/2792, was concentrated in an ultrafiltration module after removal of the fermentation residues by decantation and microfiltration. After further concentration by evaporation in vacuo, the aqueous enzyme suspension contained 700,000 PU/g. This protease concentrate was mixed with additives (3.5% by weight of sucrose, 4.5% by weight of cellulose, 3% by weight of carboxymethyl cellulose, [degree of substitution 0.65–0.75 ], 19% by weight of wheat flour, 35% by weight of corn starch and 3% by weight of polyethylene glycol, based on the mixture formed), homogenized and then converted into granules in an extruder with a cutting unit. The bore diameter of the multiple-bore extrusion die was 0.9 mm. The length-to-thickness ratio of the granules was 1:1. After spheronizing and drying of the granules, particles smaller than 0.4 mm in size and larger than 1.6 mm in size were removed by sieving. The particle fraction between 0.4 mm and 1.6 mm was coated with a solution of manganese sulfate (240 g in 460 ml of water per kg of the enzyme core) in a fluidized bed spray granulator of the STREA-1 type manufactured by Aeromatic. The following parameters were adjusted for coating:

feed air temperature: 55°–58° C.

product temperature: 36°–40° C.

waste air temperature: 32°–36° C.

air flow rate: 70 m³/h throughput of coating solution: 9.3 g/min.

Under these conditions, the water in the manganese sulfate solution evaporated from the surface of the granules and was discharged with the waste air. The manganese sulfate adhered firmly to the enzyme-containing core.

A coating suspension (285 g per kg of original enzyme core) consisting of

| | |
|---|---|
| titanium dioxide | 17% |
| technical stearyl alcohol | 19% |
| Eumulgin® RT 40ᵃ⁾ | 3% |
| water | 61% |

ᵃ⁾40x-ethoxylated castor oil, a product of Henkel KGaA was then applied in the same apparatus. The stearyl alcohol had the following C chain distribution: $C_{16}$ 0–5%, $C_{18}$ 95–100%, $C_{20}$ 0–2%, a hydroxyl value of 203 to 210 and a solidification range of 55° to 57.5° C.

To produce the coating suspension, the water was heated to around 70° C. and mixed with the liquid emulsifier. The stearyl alcohol present in solid form was stirred into and at the same time melted in the water/emulsifier solution. After addition of the titanium dioxide, a homogeneous emulsion was present in which the titanium dioxide pigment was uniformly dispersed without agglomeration. This coating suspension was sprayed onto the enzyme extrudate coated with silver corrosion inhibitor under the operating parameters mentioned above. The water in the coating suspension evaporated and was discharged with the waste air. After the coating suspension had been sprayed on, the $MnSO_4$-modified enzyme extrudates were uniformly coated with a white coloring and protective layer. The fatty alcohol formed a uniform non-porous film on the surface of the granules.

Example 2

The procedure was as in Example 1. Before application of the manganese sulfate from aqueous solution, the protease extrudate was mixed with amylase granules (Maxamyl® CXT 5000, a product of Gist Brocades, average particle size 306 μm) in a ratio by weight of 1.1:1 and coated in two stages as in Example 1. In the end product, amylase and manganese sulfate were uniformly distributed over the surface of the protease extrudate. The second coating layer protects the agglomerates against disintegration under mechanical loads and produces a uniformly white color.

We claim:

1. An enzyme containing granule, suitable for incorporation in particulate detergents, which comprises:
   (1) a core which comprises the enzyme, at least one carrier material selected from the group consisting of inorganic carrier material and organic carrier material and optionally granulation auxiliaries; and
   (2) a coating layer which comprises a silver corrosion inhibitor which is not $CoSO_4$.

2. The granule as claimed in claim 1, wherein the silver corrosion inhibitor comprises at least one member selected from the group consisting of manganese, titanium, zirconium, hafnium, vanadium, cobalt and cerium in the form of salts or complexes in which the metals are present in at least one of the oxidation stages II, III, IV, V or VI.

3. The granule as claimed in claim 1, wherein the silver corrosion inhibitor comprises at least one member selected from the group consisting of $MnSO_4$, $V_2O_5$, $V_2O_4$, $VO_2$, $TiOSO_4$, $K_2TiF_6$, $K_2ZrF_6$, $Co(NO_3)_2$ and $Ce(NO_3)_3$.

4. The granule as claimed in claim 1, which contains from 40% by weight to 95% by weight of the enzyme-containing core and 5% by weight to 60% by weight of the coating layer containing the silver corrosion inhibitor.

5. The granule as claimed in claim 1, wherein the coating layer comprises a coating system containing 45% by weight to 90% by weight of the silver corrosion inhibitor, up to 25% by weight of fine-particulate inorganic pigment, 5% by weight to 20% by weight of an alcohol, solid at room temperature, with a melting point in the range from 45° C. to 65° C., up to 5% by weight of emulsifier for the alcohol, up to 5% by weight of dispersant for at least one of the silver corrosion inhibitor and the inorganic pigment and up to 7% by weight of water.

6. The granule as claimed in claim 1 wherein the granules contain at least one member selected from the group consisting of protease, amylase, lipase and cellulase.

7. The granule as claimed in claim 1 which contains protease with an activity of 150,000 PU to 350,000 PU per gram of enzyme granules.

8. A process for the production of enzyme containing granules with an average particle size of 0.8 mm to 1.2 mm suitable for incorporation in particulate detergents which comprises:
   (1) extruding an enzyme containing composition prepared by mixing a concentrated fermentation broth containing the enzyme, optionally freed from insoluble constituents by microfiltration, with at least one carrier material selected from the group consisting of inorganic and organic carrier material to form an extrudate comprising an enzyme containing core;
   (2) optionally spheronizing the extrudate in a spheronizer;
   (3) drying the extrudate; and
   (4) applying an outer coating layer, comprising a coating system containing at least 50% by weight of silver corrosion inhibitor, up to 25% by weight of fine-particle inorganic pigment, 5% by weight to 20% by weight of alcohol, solid at room temperature, with a melting point of 45° C. to 65° C., up to 5% by weight of emulsifier for the alcohol, up to 5% by weight of dispersant for the silver corrosion inhibitor or the inorganic pigment and up to 7% by weight of water in a fluidized bed of extrudate.

9. The process as claimed in claim 8, which further comprises:
   (1) mixing with the enzyme containing core at least one particulate second enzyme under agglomeration conditions; and
   (2) applying the coating containing a silver corrosion inhibitor subsequently or simultaneously; the average particle size of the enzyme containing core being 1.1 to 3 times the average particle size of the at least one second particulate enzyme(s).

10. The process as claimed in claim 9, wherein the enzyme in the enzyme containing core comprises protease and the enzyme present in the particles which agglomerate onto the enzyme containing core comprises at least one particulate enzyme selected from the group consisting of amylase, lipase, cellulase and oxidase.

11. A particulate detergent containing the granule of claim 1.

12. A low-alkali machine dishwashing detergent containing:
   (1) from 15% by weight to 60% by weight of water-soluble builder component, from 5% by weight to 25% by weight of oxygen-based bleaching agent, from 1% by weight to 10% by weight of bleach activator, from 0.1% by weight to 10% by weight of the enzyme containing granules comprising a core, comprising at least one enzyme and at least one carrier selected from the group consisting of inorganic and organic carrier material and optionally granulation auxiliaries and a coating layer containing a silver corrosion inhibitor.

13. The granule of claim 2 which contains from 40% by weight to 95% by weight of the enzyme-containing core and 5% by weight to 60% by weight of the coating layer containing the silver corrosion inhibitor.

14. The granule of claim 1 which comprises from 50% by weight to 85% by weight of the enzyme containing core and 15% by weight to 50% by weight of the coating layer containing the silver corrosion inhibitor.

15. The granule of claim 1 wherein the coating layer comprises a coating system containing 50% by weight to 80% by weight of the silver corrosion inhibitor, 5% by weight to 20% by weight fine particulate inorganic pigment, 5% by weight to 20% by weight of an alcohol, solid at room temperature, with a melting point in the range of 45° C. to 65° C., 1% by weight to 3% by weight of emulsifier for the alcohol, 0.2% by weight to 3% by weight of dispersant for at least one of the silver corrosion inhibitor and the inorganic pigment and up to 7% by weight of water.

16. The enzyme granule of claim 1 which contains protease with an activity of from 160,000 PU to 300,000 PU per gram of enzyme granules.

17. The granule of claim 3 which contains from 40% by weight to 95% by weight of the enzyme-containing core and 5% by weight to 60% by weight of the coating layer containing the silver corrosion inhibitor.

18. The granule of claim 3 wherein the coating layer comprises a coating system containing 45% by weight to 90% by weight of the silver corrosion inhibitor, up to 25% by weight of fine-particulate inorganic pigment, 5% by weight to 20% by weight of an alcohol, solid at room temperature, with a melting point in the range from 45° C. to 65° C., up to 5% by weight of emulsifier for the alcohol, up to 5% by weight of dispersant for at least one of the silver corrosion inhibitor and the inorganic pigment and up to 7% by weight of water.

19. The granule of claim 2 wherein the granules contain at least one member selected from the group consisting of protease, amylase, lipase and/or cellulase.

20. The granule of claim 3 wherein the granules contain at least one member selected from the group consisting of protease, amylase, lipase and/or cellulase.

* * * * *